United States Patent [19]

Oelrich et al.

[11] Patent Number: 4,742,082
[45] Date of Patent: May 3, 1988

[54] SOLUTION OF LUPROSTIOL AND 1,2,-PROPANEDIOL AND METHODS OF PREPARATION AND USE

[75] Inventors: Eckhard Oelrich, Rossdorf; Carola Starz; Manfred Wotschokowsky, both of Darmstadt, all of Fed. Rep. of Germany

[73] Assignee: Merck Patent Gesellschaft mit Beschrankter Haftung, Darmstadt, Fed. Rep. of Germany

[21] Appl. No.: 901,849

[22] Filed: Aug. 29, 1986

[30] Foreign Application Priority Data

Aug. 29, 1985 [DE] Fed. Rep. of Germany ....... 3530821

[51] Int. Cl.$^4$ ............................................. A61K 31/19
[52] U.S. Cl. .................................... 514/570; 514/874
[58] Field of Search ......................................... 514/570

[56] References Cited

FOREIGN PATENT DOCUMENTS 1142434 3/1983 Canada .

OTHER PUBLICATIONS

Husa—Pharmaceutical Dispensing (Text Book), 5th ed, 1959, pp. 228, 229 & 293.

*Primary Examiner*—Leonard Schenkman
*Attorney, Agent, or Firm*—Millen & White

[57] ABSTRACT

A solution containing luprostial and 1,2-propanediol, characterized in that it contains luprostial in the form of its sodium salt in a solvent mixture comprising 50–90 percent by weight of 1,2-propanediol and 10–50 percent by weight of water, and has a pH between about 6 and 8.

17 Claims, No Drawings

SOLUTION OF LUPROSTIOL AND 1,2,-PROPANEDIOL AND METHODS OF PREPARATION AND USE

BACKGROUND OF THE INVENTION

This invention relates to an improved solution containing luprostiol and 1,2-propanediol.

Solutions of luprostiol (7α-(2-(3-(3-chlorophenoxy)-hydroxypropylthio)-3α, 5α-dihydroxycyclopentyl)-5-heptenoic acid) in 1,2-propanediol are disclosed in Canadian Patent Specification No. 1,142,434. They are used in particular, as injection solutions in medical treatment of humans and, above all, in veterinary medicine, for luteolysis, for synchronizing estrus or for inducing labor, for example in the case of horses, cattle, pigs, sheet and goats.

Disadvantages have been found in using the known solutions. In particular, problems are caused by the high viscosity, which renders drawing and injection considerably difficult, particularly at low temperatures such as prevail in the winter half-year, which is the principal season for practical use. Furthermore, solutions of the free acid luprostiol are unstable to a limited extent, since esters are formed from the acid and the solvent as the result of acid autocatalysis.

OBJECTS OF THE INVENTION

It is an object of this invention to avoid, or at least to mitigate, these disadvantages of the known Luprostiol solutions.

Another object is to provide a luprostiol solution of low viscosity which is stable from the chemical and pharmaceutical aspects.

Another object is to provide a Luprostiol solution which permits an adequately high concentration of active compound and for which the local tolerance is good.

It is another object of the invention to provide a method of preparing a solution containing the sodium salt of luprostiol in a solvent mixture of 50 to 90 percent by weight 1,2-propanediol and 10 to 50 percent by weight water.

Another object of the invention is to provide a methodo for inducing labor in mammals.

Another object of the invention is to provide a method for inducing luteolysis in mammals.

Furthermore, another object of the invention is to provide a method for synchronizing estrus in mammals.

Upon further study of the specific and appended claims, further objects and advantages of this invention will become apparent to those skilled in the art.

SUMMARY OF THE INVENTION

These objects are achieved by providing a solution containing luprostiol sodium salt dissolved in a solvent mixture comprising, based on the total solvent mixture, about 50–90 percent by weight 1,2-propanediol and 10–50 percent by weight water, said solution having a pH of about 6–8.

This improved solution is stable from the chemical and pharmaceutical aspects, is self-preserving and has a substantially lower viscosity than the known luprostiol solutions, so that, as far as viscosity is concerned, it can be handled with few if any problems at any temperature customary in practice. In addition, the local tolerance for the solution is better than that for conventional luprostiol solutions, The solution according to the invention preferably contains 0.1 to 100, preferably 1 to 10 and especially 3 to 8 mg of luprostiol sodium salt per ml.

The solvent mixture contains 50 to 90, preferably 60 to 80 and especially 65 to 75, per cent by weight of 1,2-propanediol and, accordingly, 10 to 50, preferably 20 to 40 and especially 25 to 35, percent by weight of water.

When the water content is higher than 50 percent, luprostiol or its sodium salt may precipitate.

The pH of the solution is between about 6 and 8, preferably between 6.5 and 75 and especially between 6.8 and 7.2.

At pH values lower than 6 and higher than 8, the chemical and galenical stability as well as the compatibility of the solution will decrease.

The invention also relates to a process for the preparation of a solution containing luprostiol and 1,2-propanediol, characterized in that luprostiol or preferably its sodium salt is dissolved in 1,2-propanediol and the concentration of the solution is then adjusted by the addition of water. If appropriate, additional 1,2-propanediol cn be added in order to obtain a solvent mixture which has the desired concentrations of 50–90 percent by weight of 1,2-propanediol and 10–50 percent by weight of water. If necessary, the pH of the solution can be adjusted to the desired value of between about 6 and 8 by adding a basic sodium compound.

Preferably, the solution of the invention is prepared by the following procedure: (1) a solution of approximately 12% of 13% luprostiol in 1,2-propanediol is prepared; (2) the calculated amount of water and, if necessary, additional 1,2-propanediol are added to the solution; (3) if necessary, the pH of the solution is adjusted to within the desired range by adding sodium hydroxide solution; and (4) if necessary, addition 1,2-propanediol is added to the solution to achieve the desired concentration of the solvent mixture components.

This procedure avoids a precipitation of luprostiol or its sodium salt.

Examples of basic sodium compounds which are also suitable instead of sodium hydroxide solution are sodium carbonate or bicarbonate, preferably in the form of their aqueous solutions.

The operations described up to this point are preferably carried out at temperatures between 10° and 80° C., preferentially between 20° and 30° C., and advantageously with stirring.

The solution thus obtained is preferably subjected to sterile filtration under aseptic conditions and, if desired, under an inert gas, such as nitrogen, through a membrane filter having a pore width of 0.1 to 0.4 $\mu$m, preferably 0.2 $\mu$m. The low viscosity of the solution enables it to be filtered more rapidly than the known solution of higher viscosity. Thus, the low viscosity provides a saving of time in the preparation, a briefer and hence smaller exposure of the active compound and a shorter time for the possible absorption of impurities.

The resulting solution can be filled into ampules or injection vials, preferably under aseptic conditions and protected from light. The stock vessels can be evacuated and filled with an inert gas, such as nitrogen. Each ampule or injection vial can contain, for example, between 0.1 and 1,000, preferably between 0.5 and 100, mg of active compound.

The new solution can be used for medical treatment of mammals, including humans, for luteolysis, synchronizng estrus, and inducing labor. It is preferably administered parenterally as an injection solution, in particular by intramuscular or intravenous injection, but can also be administered orally, for example in the form of drops. It is preferably administered in a dosage of 0.001 to 1, in particular 0.005 to 0.1 mg of active compound per kg of body weight. The dosage depends on the species treated, the mode of administration and the purpose of treatment. The dosage can therefore also fall below or exceed the values indicated above.

If it is desired, for example, to utilize the estrus synchronizing action of luprostiol, it is particularly advantageous to administer, for example to cattle (cows or heifers), 0.1 mg to 20 mg, preferably 0.5 mg to 15 mg and especially 1.5 mg to 10 mg, of the active compound by intramuscular injection. It is favorable to administer the effective dose by a single injection between the 7th day and the 12th day of the menstrual cycle, but is is also possible to inject part doses several times, and, if appropriate, distributed over several days. Estrus can be synchronized by administering luprostiol in the case of other animals too, for example in the case of dogs, horses, sheep and pigs. The effective dose then varies, depending on the average body weight of the species treated, and can be determined withoout difficulty by those skilled in the art with the aid of the guiding values indicated above for cattle.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLE 1

600 g of 1,2-propanediol and 298.8 g of water for injection purposes are added successively to 60.19 g of a 12.46 percent solution of luprostiol in 1,2-propanediol, and the mixture is stirred until a clear solution is available. The pH of this solution is adjusted to a value of 7.0 with 16.7 ml of 1 M sodium hydroxide solution. The solution is made up with 1,2-propanediol to a final weight of 1,048 g = 1,000 ml, subjected to sterile filtration through a membrane filter under aseptic conditions and filled into 10 ml injection vials. One ml of this injection solution contains 7.5 mg of luprostiol. Viscosity: 14 mPas at 20°, 44 mPas at 0°. (In comparison, a solution of 7.5 mg/ml of luprostiol in pure 1,2-propanediol has the following viscosity values: 61 MPas at 20°, 257 MPas at 0°).

EXAMPLE 2

650 g of 1,2-propanediol, 313.7 g of water for injection purposes and 6.7 ml of 1 M sodium hydroxide solution are added, analogously to Example 1, to 23.47 g of a 12.78 percent solution of luprostiol in 1,2-propanediol, and the mixture is then made up with 1,2-propaediol to a final weight of 1,045 g=1,000 ml. The solution, which has a pH of 7.0, is filtered under sterile conditions and filled into 10 ml injection vials. One ml of this injection solution contains 3.0 mg of luprostiol.

EXAMPLE 3

1,000 ml of an injection solution containing 7.5 mg/ml of luprostiol are obtained, analogously to Example 1, from 55.8 g of a 13.5 percent solution of luprostiol in 1,2-propanediol, 404.5 g of water for injection purposes, 570.6 g of 1,2-propanediol and 16.1 g of 1 M sodium hydroxide solution. Viscosity: 10.1 mPas at 20°, 29.4 mPs at 0°.

The preceding examples can be repeated with similar success by substituting the operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a solution containing luprostiol and 1,2-propanediol, the improvement wherein said solution contains luprostiol sodium salt dissolved in a solvent mixture comprising, based on the total solvent mixture, about 50-90 percent by weight 1,2-propanediol and about 10-50 percent by weight water, said solution having a pH of about 6-8.

2. The solution of claim 1 wherein the solution contains about 0.1-100 mg of luprostiol sodium salt per ml.

3. The solution of claim 2 wherein the solution contains about 1-10 mg of luprostiol sodium salt per ml.

4. The solution of claim 3 wherein the solution contains about 3-8 mg of luprostiol sodium salt per ml.

5. The solution of claim 1 wherein the solvent mixture comprises about 60-80 percent by weight 1,2-propanediol and about 20-40 percent by weight water.

6. The solution of claim 5 wherein the solvent mixture comprises about 65-75 percent by weight 1,2-propanediol and 25-35 percent by weight water.

7. The solution of claim 1 wherein the pH of the solution is about 6.5-7.5.

8. The solution of claim 7 wherein the pH of the solution is about 6.8-7.2.

9. A method of preparing a solution containing luprostiol in a solvent mixture of 1,2-propanediol and water comprising the steps of:
(a) dissolving Luprostiol acid or its sodium slt in 1,2-propanediol to form a solution,
(b) adjusting the concentrations of the solvent mixture components by adding water to the solution of step (a) so that the solvent mixture comprises, based on the total solvent mixture, about 50-90 percent by weight 1,2-propanediol and 10-50 percent by weight water, wherein the pH of the solution is about 6-8.

10. The method of claim 9 wherein step (b) also includes adding 1,2-propanediol to adjust the concentrations of the solvent mixture components so that the solvent mixture comprises 50-90 percent by weight 1,2-propanediol and 10-50 percent by weight water.

11. The method of claim 9 wherein step (b) also includes adjusting the pH of the solution to about 6-8 by adding a basic sodium compound.

12. The method of claim 11 wherein said basic sodium compound is sodium hydroxide.

13. A process for inducing labor in mammals comprising administering a labor inducing amount of the solution recited in claim 1.

14. A process for inducing luteolysis in mammals comprising administering a luteolysis inducing amount of the solution recited in claim 1.

15. A process for synchronizing estrus in mammals comprising administering an effective amount of the solution recited in claim 1 to animals having unsynchronized estrus.

16. An ampule containing the solution recited in claim 1 in an aseptic form.

17. An injection vial containing the solution recited in claim 1 in aseptic form.

* * * * *